United States Patent
Lin et al.

[11] Patent Number: 6,151,971
[45] Date of Patent: Nov. 28, 2000

[54] GAS SAMPLING DEVICE

[75] Inventors: Yao Min Lin; Yung Hsin Chen, both of Hsinchu; Jack Chen, Taipei, all of Taiwan

[73] Assignee: Industrial Technology Research Institute, Hsinchu, Taiwan

[21] Appl. No.: 09/219,012

[22] Filed: Dec. 23, 1998

[30]  Foreign Application Priority Data

Jun. 29, 1998 [CN] China .................................. 87210419

[51] Int. Cl.7 ....................................................... G01N 1/00
[52] U.S. Cl. ....................................................... 73/863.23
[58] Field of Search ............................. 73/863.23, 31.02; 356/437, 440

[56]  References Cited

U.S. PATENT DOCUMENTS 5,163,332  11/1992  Wong .
5,195,356  3/1993  Stavinoha .
5,291,265  3/1994  Kebabian .
5,340,986  8/1994  Wong .

*Primary Examiner*—Robert Raevis
*Attorney, Agent, or Firm*—Kenyon & Kenyon

[57]  ABSTRACT

A gas sampling device comprises an elongated tube having a plurality of holes on the wall thereof a porous mesh surrounding the outer surface of said tube, a light source located at one end of said tube, a light sensor located at the other end of said tube, a first housing mounted at the one side of the tube for holding said light source, a second housing mounted on the other end of the tube for holding said light sensor, and a gas flowing channel formed in at least one of said first and second housing for communicating the interior and said the exterior of the tube thereby producing an action of thermal convection to promote the concentration of the gas in the interior of the tube to reach a stable balance condition rapidly.

4 Claims, 2 Drawing Sheets

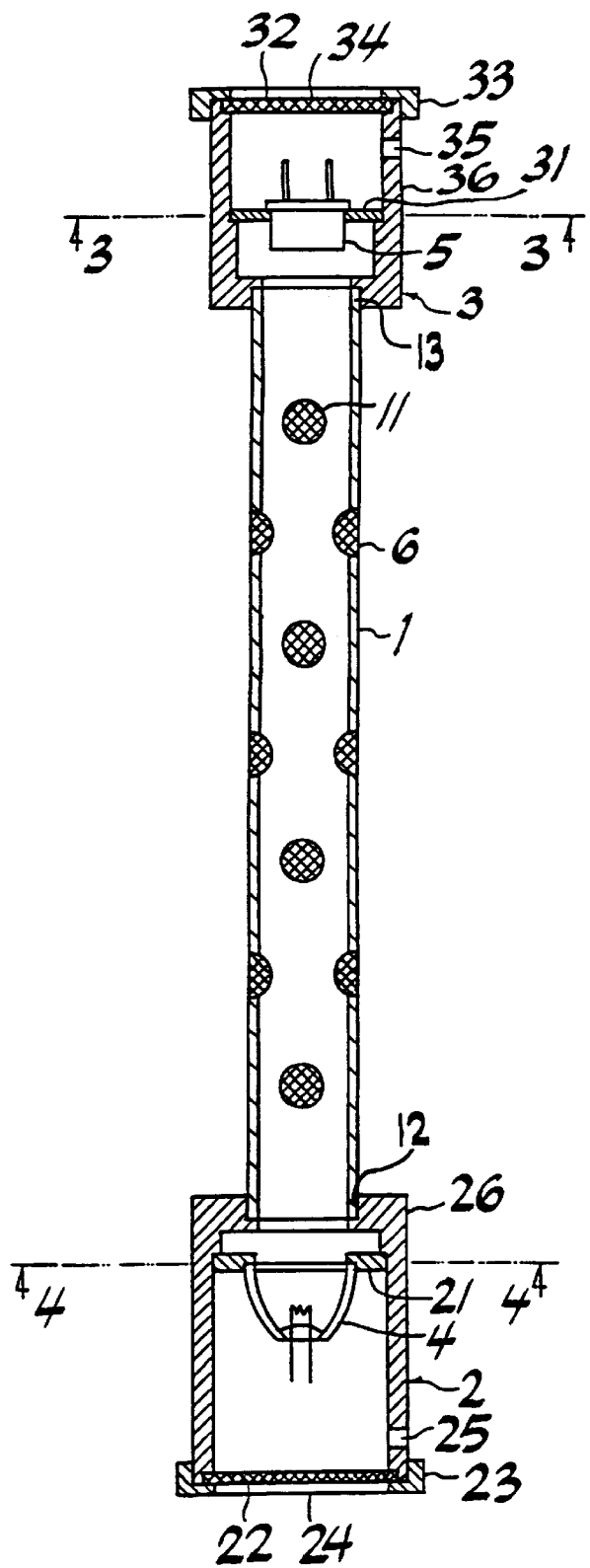
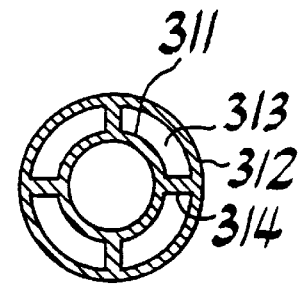
Fig. 3
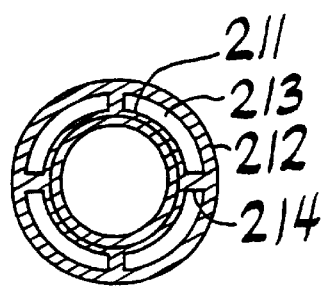
Fig. 4
Fig. 2

GAS SAMPLING DEVICE

BACKGROUND OF THE INVENTION

1. Field of the Invention

The present invention relates to a gas sampling device, particularly to one utilized in a Non-Dispersive Infrared (NDIR) gas concentration analysis instrument.

2. Related Prior Art

A "Non-Dispersive Infrared gas concentration analysis instrument" is operated in accordance with the principle that some specific gases have specific spectrums in the range of infrared frequency. For example, $CO_2$ has a characteristic that a light at a wavelength of 4.3 micrometer will be absorbed thereby.

As shown in FIG. 1, a conventional gas sampling device comprises a columnar or square tube 51 which is used as a sampling means and is provided with many holes 52 on the wall thereof so as to permit gas to freely diffuse. The concentration of the gas existing, in the interior and exterior of the tube will reach a balanced condition via the holes due to the concentration difference and the principle of free diffusion. Moreover, a porous mesh 53 is provided on the outer surface of the tube to envelope the holes so as to prevent dust from entering the tube. A light source 54 and a light sensor 55 are also provided respectively on two sides of the tube for permitting, light emitted and detected at a specific range. In operation, the light to be emitted from the light source 54 goes through the interior of the tube and then is detected by the light sensor 55 which detects the intensity of the received infrared-light at a specific wavelength and outputs an electric signal representing the gas concentration.

However, since the diffusion speed of gas is proportional to the concentration difference, the increasing rate for the concentration of the gas in the tube will be faster at the beginning of sampling, and the diffusion rate will be slower as the concentration difference between the interior and the exterior of the tube reduces. Thus, it needs a longer time to reach a balance condition in a higher concentrated form.

SUMMARY OF THE INVENTION

It is an object of this invention to provide an improved gas sampling device that accelerates the completion of a concentration balance so as of provide rapid detection to the concentration of the gas.

To meet the above objective, a gas sampling device in accordance with this invention comprises an elongated tube having a plurality of holes on the wall thereof, a porous mesh enveloping the outer surface of the tube, a light source located on one side of the tube for emitting infrared rays into the interior of the tube, a light sensor located on the other side of the tube for detecting light at a specific spectrum, a first housing for holding the light source at one end of the tube, and a second housing for holding the light sensor at the other end of the tube, and is characterized in that at least one of the first and second housings is provided with at least one vent hole allowing communication between the interior and the exterior of the tube.

According to one aspect of the present invention, when the gas sampling device is standing vertically with the vent hole being on the top side of the tube, the gas first entering into the interior of the tube will be heated by the emission of the light source and will move upward and flows outward from the vent hole located on the top side of the tube. Due to convection action as thermal the heated gas is vented from the tube, new cold gas will enter into the interior of the tube via the holes provided on the wall and the lower end of the tube and thus causing the gas to circulate. By means of the gas circulation and natural diffusion, the gas concentration inside and outside the gas sampling device will rapidly reach a balanced condition.

BRIEF DESCRIPTION OF DRAWINGS

FIG. 2 is a part of a cross section view of a gas sampling device according to one embodiment of the present invention;

FIG. 3 is a cross-section view of the light sensor bracket of FIG. 2 along the line II;

FIG. 4 is a cross-section view of the light sensor bracket of FIG. 2 along the line III.

DETAILED DESCRIPTION OF PREFERRED EMBODIMENTS

Figure 1:
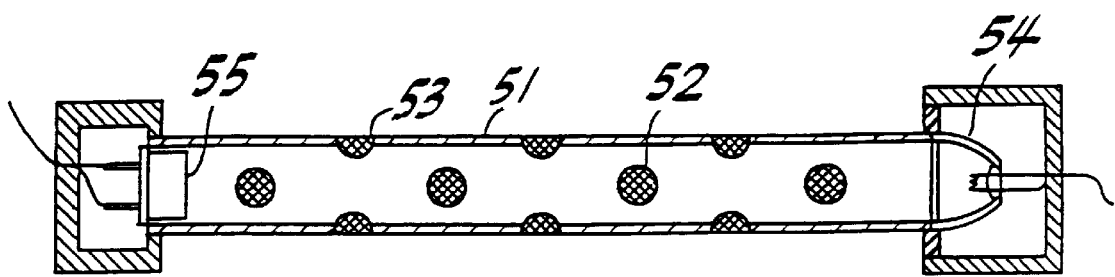
FIG. 1 is a cross-section view of a conventional gas sampling device.

FIG. 2 illustrates a part of a cross-section view of a gas sampling device according to a preferred embodiment of the present invention. Referring to FIG. 2, a gas sampling device in accordance with this invention generally comprises an elongated sampling tube 1 having a plurality of holes 11 on the wall thereof, a porous mesh 6 surrounding the outer surface of the tube 1, a light source 4 located on one side of the tube 1 for light the interior of the tube 1, a light sensor 5 located on the other side of the tube 1 for detecting the light of a specific spectrum, a first housing 2 mounted on one end of the tube for holding the light source 4, and a second housing 3 mounted on the other end of the tube 1 for holding the light sensor 5.

The first housing 2 comprises a first shell 26 and a bracket 21. The first shell 26 has a first end face which is engaged with the one end 12 of the sampling tube 1 and has a first opening 27 formed thereon for communicating with the interior of the tube 1 and a second end face provided with a vent hole 24, serving as a second opening. The bracket 21 is allocated inside the first shell 26 for holding the light source 4. The second housing 3 similarly comprises a second shell 36 and a bracket 31. The second shell 36 has a first end face engaged with the other end 13 of the sampling tube and having a first opening 37 communicating with the interior of the tube 1, and a second end face which is provided with a vent hole 34, serving as a second opening. The bracket 31 is allocated inside the second shell 36 for holding the light sensor 5.

Referring to FIGS. 3 and 4, the bracket 21 comprises an inner ring 211 for holding the light source 4, a concentric outer ring 212 for engaging with the first shell 26, and a plurality of ribs 214 firmly connecting the inner ring 211 and the outer ring 212 so as to fix the light source 4 on the first shell 26 as well as to form a plurality of vent holes 213 between the light source 4 and the first shell 26. The bracket 31 similarly comprises an inner ring 311 for holding the light sensor 5, a concentric outer ring 312 for engaging with the second shell 36, and a plurality of ribs 314 fly connecting the inner ring 311 and the outer ring 312 so as to fix the light sensor 5 on the second shell 36 as well as to form a plurality of vent holes 313 between the light sensor 5 and the second shell 36. The vent holes 24,213 and 34,313 and the first openings 27,37 as well as the space between the light sensor 5 or the light source 4 with the shells 26, 36 respectively constitute a gas exhaust channel communicating the interior of the sampling tube and the exterior thereof.

Referring back to FIG. 2, the vent holes 24,34 of the first and the second shells 26,36 are covered with porous meshes 22,32 respectively. The porous meshes 22,32 are held by fixing rings 23,33 snapping into the second end faces of the shells 26,36 respectively. Furthermore, the shells 26,36 are respectively provided with openings 25,35 on their side wall so that signal wires or the like can pass therethrough.

The use of the gas sampling device according to the invention is described as follow. The gas sampling device 1 is standing vertically in a detecting space, with the light sensor 5 being in the upper position. Due to a diffusion action, the gas existing in the space will enter the interior of the sampling tube 1 via the holes 11 and thereby filling up the interior of the sampling tube 1. When the light source 4 is powered on, the gas existing in the interior of the tube I will be heated by the light emitted from the light source 4, and thus converts into heated gas, which in turn moves upward and flows to the exterior of the tube I through the vent holes 313,34 provided in the housing 3.

Furthermore, due to the exhaust of the heated gas from the tube 1, the gas outside the sampling tube 1 will flow into and fill up the interior of the tube 1 and thus thermal convection is formed due to a pressure difference between the interior and the exterior of the tube 1. In accordance with the above, it can be confirmed that the rate of interchanging the gas existing in the interior and exterior of the tube according to this invention will be faster than that of a conventional sampling tube. The gas concentration inside the tube 1 stablizes quickly soon and thus a further test can be performed.

However, the foregoing description of the preferred embodiment of this invention is presented only for the purpose of illustration and description. It is not intended to be exhaustive nor to limit this invention to the precise form disclosed. Many modifications and variations are possible in light of the above teaching. Therefore, it is intended that the scope of this invention should be limited not by this detailed description, but rather by the claims appended hereto.

What is claimed is:

1. A gas sampling device comprising an elongated tube, a first housing, a second housing, a light source, and a light sensor, the elongated tube having two ends and a plurality of holes formed thereon for interiorly sampling gas, the light source being held by the first housing for emitting light toward the second housing through the gas sampled in the interior of the tube, and the light sensor being held by the second housing for receiving the light emitted from the light source, and wherein the first and the second housings are secured at the two ends of the tube respectively, at least one of the first and the second housings being formed with a gas exhaust channel communicating the exterior thereof and the interior of the tube so that the gas sampled in the interior of the tube will escape there-through when the sampled gas is heated by the light source.

2. The gas sampling device of claim 1, wherein the at least one housing includes a shell and a bracket, the shell having a first end face engaged with the one end of the tube and having a first opening formed thereon for communicating with the interior of the tube, the bracket being located inside the shell for holding one of the light source and the light sensor.

3. The gas sampling device of claim 2 wherein the shell further has a second end face formed with a second opening which, together with the first opening and the space between the one of the light source and the light sensor with the shell, define the gas exhaust channel.

4. The gas sampling device of claim 3, wherein the at least one housing further comprises a porous mesh covering the second opening and a fixing ring for holding the porous mesh on the shell thereof.

* * * * *

UNITED STATES PATENT AND TRADEMARK OFFICE
CERTIFICATE OF CORRECTION

PATENT NO. : 6,151,971  
DATED : November 28, 2000  
INVENTOR(S) : Lin et al.

Page 1 of 1

It is certified that error appears in the above-identified patent and that said Letters Patent is hereby corrected as shown below:

Column 1,
Line 40, change " ... balance ..." to -- balanced -- .
Line 45, change " ..." to ..." to -- of -- .
Line 66, change "... to convection action as thermal the heated gas ..." to -- to thermal convection action, as the heated gas -- .

Column 2,
Line 2, delete "and".

Column 3,
Line 15, change " ... I ..." to -- I -- .
Line 29, delete "soon" .

Signed and Sealed this

Fourth Day of September, 2001

*Attest:*

NICHOLAS P. GODICI
*Attesting Officer*  *Acting Director of the United States Patent and Trademark Office*